United States Patent [19]

Northemann

[11] Patent Number: 5,672,794
[45] Date of Patent: Sep. 30, 1997

[54] RECOVERY OF STYRENE FROM WASTE POLYSTYRENE

[75] Inventor: Andreas Northemann, Ludwigshafen, Germany

[73] Assignee: BASF Aktiengesellschaft, Ludwigshafen, Germany

[21] Appl. No.: 697,718

[22] Filed: Aug. 29, 1996

Related U.S. Application Data

[63] Continuation of Ser. No. 319,653, Oct. 7, 1994, abandoned.

[30] Foreign Application Priority Data

Oct. 21, 1993 [DE] Germany ............... 43 35 972.8

[51] Int. Cl.$^6$ .................. C07C 4/22; C07C 1/00
[52] U.S. Cl. ............. 585/241; 585/240; 585/832
[58] Field of Search .................. 585/241, 240, 585/832, 242

[56] References Cited

U.S. PATENT DOCUMENTS

| | | | |
|---|---|---|---|
| 3,901,951 | 8/1975 | Nishizaki | 585/241 |
| 4,429,172 | 1/1984 | Zellerhoff et al. | 585/241 |
| 5,264,640 | 11/1993 | Platz | 585/241 |
| 5,369,215 | 11/1994 | Platz | 585/241 |

FOREIGN PATENT DOCUMENTS

| | | |
|---|---|---|
| 502618 | 9/1992 | European Pat. Off. |
| 577279 | 1/1994 | European Pat. Off. |
| 30 37 829 | 8/1983 | Germany |
| 92/04423 | 3/1992 | WIPO |

OTHER PUBLICATIONS

Recent Developments in the Thermal Degradation . . . , Guyot, Poly. Degrad. Stab. 15 (1986) 219–235.
Japanese Abstract J 4 9005-183.
Soviet Union Abstract SU 771-079.
Japanese Abstract J 2029-492.
Study on Thermal Degrad. . . , Ohtani et al., Eur. Polym. J. vol. 26, No. 8, pp. 893–899, 1990.
Database WPI, Derwent Publications Ltd., AN 84–197547 [32] (English abstract of JP-A 59 111 815).

Primary Examiner—Glenn A. Caldarola
Assistant Examiner—Bekir L. Yildirim
Attorney, Agent, or Firm—Keil & Weinkauf

[57] ABSTRACT

Monomeric styrene is recovered from plastics waste containing styrene polymers by thermal depolymerization by a process in which the waste is transported in liquid or solid form into a fluidized bed of a solid heat transfer agent and is cracked or depolymerized in an average residence time of less than 60 seconds and styrene is obtained from the gaseous crack products. Preferably, magnesium aluminum silicate is used as a heat transfer agent and $C_1$–$C_6$-hydrocarbons formed as byproducts in the depolymerization are used as operating gas for maintaining the fluidized bed and are circulated.

4 Claims, No Drawings

RECOVERY OF STYRENE FROM WASTE POLYSTYRENE

This application is a continuation of application Ser. No. 08/319,653, filed on Oct. 7, 1994, abandoned.

The thermal degradation of polystyrene to monostyrene (depolymerization) is generally known and is described in many publications, for example by A. Guyot in Polym. Degrad. Stabil. 15(3) (1986), 219–235, or by H. Ohtani et al. in Eur. Polym. J. 26(8) (1990), 893–899.

According to DE-A-3 037 829, modified pitches and low-boiling aromatics can be obtained by thermal treatment of plastics wastes which contain polymeric styrene. This is effected in the presence of high-boiling aromatics, the waste being added to the liquid high-boiling aromatics and at the same time the resulting low-boiling aromatics being separated off.

JA-A-74 05 183 discloses that 37.5 parts of polystyrene can be dissolved in 62.5 parts of solvent and distillation can be carried out at 600° C. with decomposition. In this procedure, styrene is obtained in a yield of about 80%, based on polystyrene used.

A possible gentle method for heating such polystyrene solutions comprises the addition of steam:

SU-A-771 079 describes a process in which the polystyrene is dissolved in an organic solvent in a ratio of from 1:6 to 1:10 and then thermally degraded in the presence of steam. The steam is added in a ratio of 1:1 relative to the polystyrene. About 77% of styrene is obtained, about 80% of the starting material being converted.

Furthermore, SU-A-1035 017 describes a process for the depolymerization of polystyrene in the presence of steam. Here, a catalyst, ie. iron chromium potassium oxide, is used. The polymer material is dissolved and is passed together with steam (3:1 relative to the polymer) over the catalyst. The ratio of solvent to polymer is about 1:1. The yield of monomer is said to reach about 85%, based on polymer material used.

JA-A-2 029 492 describes a process in which polystyrene in liquid form is thermally degraded and the escaping, low-boiling components are condensed in the gas phase over a zeolite to give hydrocarbons carbons and aromatic compounds.

GB-A-2 228 493 describes a process for recovering styrene by pyrolytic reduction of polystyrene waste. In this mixed catalytic/thermal liquid-phase and gas-phase process, styrene is obtained in an amount of about 70–75% and a lead/zinc alloy is required as a heat transfer agent.

All known processes have disadvantages: it is sometimes necessary to dissolve the waste polystyrene before the depolymerization. The large amounts of solvent make such a process unprofitable since the solvent must be recovered. Other processes are divided into two steps, thermal degradation and catalytic cracking of the degradation products. Furthermore, some processes use catalysts which are rapidly deactivated so that steam is additionally required to counteract this in the depolymerization.

It is an object of the present invention to provide a process which does not have the abovementioned disadvantages.

We have found that this object is achieved by a process for recovering covering monomeric styrene from plastics waste containing styrene polymers by thermal depolymerization, wherein, according to the invention, the waste in liquid or solid form is transported into a fluidized bed of a solid heat transfer agent heated to 400°–700° C. and is cracked or depolymerized in an average residence time of less than 60 seconds and styrene is obtained from the gaseous crack products.

A heat-stable material which is inert under reaction conditions and advantageously has a particle size of 30–500 µm, preferably 70–350 µm, is used as the heat transfer agent. Magnesium aluminum silicate has proven useful. The depolymerization of polystyrene takes place purely thermally so that no catalyst is required for the reaction.

A suitable material has a fluidization point of 0.02–0.07, preferably 0.03–0.06, m/s. To check whether it is actually an inert material, pure styrene can be transported through the fluidized bed. The styrene should be recovered in a yield of at least 99%.

A gas which is inert under the reaction conditions is used to fluidize the bed. This may be hydrogen, nitrogen, a noble gas, carbon dioxide or steam or gaseous compounds formed in the reaction. The gaseous compounds formed in the reaction are preferably used and in this case are circulated.

In the preferred embodiment, the waste is metered in liquid or solid form into the fluidized bed. If solid polystyrene is transported into the fluidized bed, the residence time must be substantially increased. The polystyrene is preferably melted and the melt pumped into the reactor. Expanded polystyrene is first degassed in an appropriate mill. The polystyrene may be melted without prior shredding or comminution. For example, an extruder is suitable for melting and metering the polystyrene, but any other method of melting and transporting the polystyrene may also be used.

A particular advantage of the process is that the polystyrene is transported into the reactor in undiluted form as a melt and that no further apparatus must be used for dissolution. Moreover, this procedure permits a higher space-time yield than the known processes.

The internal temperature of the reactor should be 400°–700° C. A higher temperature is possible but promotes the formation of low molecular weight gaseous substances. At lower temperatures, the rate of the depolymerization reaction decreases sharply; the process is then generally less cost-efficient. A temperature range of from 450° to 650° C. is particularly preferred.

The depolymerization of the polystyrene is preferably carried out at atmospheric pressure but may also take place at above or below atmospheric pressure.

The residence time in the reactor is established by the stream of fluidizing gas. It is generally less than 60, for example from 0.5 to 40, preferably from 2 to 25, seconds. The residence time is determined by the size of the reactor used and by the fluidization point of the fluidized material present in the reactor. The residence time plays an important role, particularly in the method of metering. When solid polystyrene is metered, the residence time is, for example, about 30 seconds, whereas the residence time in the case of liquid metering tends to be 4 to 10 seconds.

In the preferred embodiment, the gas stream leaving the fluidized bed reactor is condensed in two stages in order to achieve preliminary separation of certain boiling fractions. A first condenser is operated at above the boiling point of styrene, preferably at 160°–200° C. A downstream second condenser is operated at a considerably lower temperature, preferably at up to 40° C., in order to separate off the components which are liquid at this temperature.

The components which are still gaseous in this low temperature range are circulated, with the aid of a compressor, for fluidization of the bed. Only a small excess is removed and is used, for example, for energy generation. The fraction separated off in the first condenser between the boiling point of styrene and 200° C. is recycled to the process. This part furthermore serves to provide the energy required for the total process, this being achieved by the combustion of some of this fraction. The energy required for the process depends to a great extent on the space-time behavior of the plant. In the preferred procedure, the amount of condensate used to cover the energy requirement is 50–100% of the fraction separated off between the boiling point of styrene and 200° C. From the fraction which boils at from 100° to 170° C. and essentially contains the monomeric styrene, the styrene can be obtained by distillation and can be reused.

In the preferred embodiment of this process, all fractions and streams obtained are used. By using some fractions which contain no monomeric styrene for energy generation, the process can be operated independently in terms of energy, ie. without connection to existing chemical plants and hence economically. This process thus makes a valuable contribution to the recycling of polystyrene waste.

EXAMPLE 1

As an illustration of the laboratory scale, 1340 g or 0.93 liter of magnesium aluminum silicate having a particle size of 150–250 µm and a fluidization point of 0.047 m/sec are introduced into a steel fluidized-bed reactor having an internal diameter of 7 cm and a height of 30 cm and are heated to 550° C. by means of an internal heat exchanger. Previously melted polystyrene waste which contains 90% of styrene, calculated as monomer, is pumped into the reactor at a rate of 0.2 kg/h. 140 l (S.T.P.)/hour of gas are blown into the reactor for fluidization of the bed, the resulting residence time being 4 seconds. The gas stream leaving the reactor is condensed in two stages. The first condenser is operated at 170° C. for separating off relatively high-boiling components, and the second condenser is operated at 20° C. for separating off the styrene. By means of a compressor, the noncondensable fraction is used for fluidization of the bed. The two condensed fractions are collected over a period of 10 hours and are then analyzed.

In the condenser operated at 170° C., 187 g (9.4%, based on material used) of a fraction which consists of an undetermined mixture of dimeric styrene, trimeric styrene and higher-boiling waxy substances are separated off. In the condenser operated at 20° C., 1720 g (86%, based on material used) are deposited, this material consisting of 87% by weight of styrene, 5% by weight of ethylbenzene and toluene, 5% by weight of methylated styrene derivatives and 3% by weight of unidentified aromatics. This corresponds to a styrene yield (based on polymer used) of 84%.

The gas fraction, which accounts for 5.6% by weight, based on material used, and essentially consists of $C_1$–$C_6$-hydrocarbons, is circulated for fluidization of the bed.

EXAMPLES 2–6

The procedure corresponds to the general method of Example 1, the temperature and residence time being systematically varied. The table below shows the results.

TABLE

| | Polystyrene Content | | | Residence | Running | | Yield | | |
|---|---|---|---|---|---|---|---|---|---|
| Ex. | SW[1] % by wt. | Feed g/h | Temp. °C. | time sec | time h | Fraction 1 % by wt. | Fraction 2 % by wt. | Styrene %[2] | Gas |
| 2 | 90 | 150 | 550 | 4 | 10 | 10.1 | 85.2 | 79 | 4.7 |
| 3 | 85 | 200 | 600 | 5 | 10 | 7.8 | 85.5 | 82 | 6.7 |
| 4 | 85 | 300 | 600 | 5 | 10 | 7.5 | 86.3 | 85 | 6.2 |
| 5 | 90 | 300 | 650 | 3 | 10 | 6.7 | 87 | 83 | 6.3 |
| 6 | 85 | 300 | 650 | 5 | 10 | 5.3 | 86.8 | 86 | 7.9 |

[1]Styrene content of waste used
[2]Yield of styrene in the fraction condensed at 20° C., based on the monomer content of the waste used

EXAMPLE 7

The procedure is carried out under the conditions of Example 6 and the productivity of the process is determined over a longer period. The running time of the experiment is 1000 h. During this time, 30 kg of polystyrene waste are depolymerized. 23.2 kg of styrene (yield 86%) are obtained from the waste, which consisted of 90% of polymerized styrene. The fraction condensed at 170° C., which accounted for 5.1% by weight of the amount of polymer used and had a calorific value of 41 MJ/kg, is used for energy generation, and the gas fraction is circulated for fluidization of the bed.

We claim:

1. A process for recovering monomeric styrene from plastics waste containing styrene polymers by thermal depolymerization, wherein the waste in liquid or solid form is transported into a fluidized bed of magnesium aluminum silicate heated to 400°–700° C. and is cracked or depolymerized in an average residence time of less than 60 seconds and styrene is recovered from the gaseous crack products.

2. A process as claimed in claim 1, wherein $C_1$–$C_6$-hydrocarbons formed as byproducts in the depolymerization are circulated as operating gas for maintaining the fluidized bed.

3. A process as claimed in claim 1, wherein the condensation of the crack products is carried out in two or more stages, a first condensation stage at from 160°–200° C. and a second stage at up to 40° C. being provided and styrene being obtained from the second condensation stage.

4. A process as claimed in claim 1, comprising a fluidization point of 0.02–0.07 m/s or a particle size of 300–500 µm.

* * * * *